United States Patent [19]
Wakasugi et al.

[11] Patent Number: 5,811,555
[45] Date of Patent: Sep. 22, 1998

[54] METHOD FOR SUBSTITUTION OF AN AMINO GROUP OF A PRIMARY AMINE BY A CHLORINE ATOM AND A SYNTHETIC METHOD BY APPLICATION THEREOF

[75] Inventors: Takashi Wakasugi; Tadashi Miyakawa; Takayuki Tanonaka, all of Fukushima, Japan

[73] Assignee: Kureha Chemical Industry Co., Ltd., Tokyo, Japan

[21] Appl. No.: 749,775

[22] Filed: Nov. 20, 1996

[30] Foreign Application Priority Data

Nov. 22, 1995 [JP] Japan .................................. 7-328061

[51] Int. Cl.$^6$ ................................................. C07D 277/32
[52] U.S. Cl. ............................................................... 548/202
[58] Field of Search ................................................. 548/202

[56] References Cited

U.S. PATENT DOCUMENTS 3,461,125  8/1969  Kollonitsch ............................ 548/202

FOREIGN PATENT DOCUMENTS 0260560  3/1988  European Pat. Off. .
0446913  9/1991  European Pat. Off. .

OTHER PUBLICATIONS

Nagahara, J. Med. Chem. 33 (1) 407, 1990.
McLean, John, "Reactions of Certain Thiazoles and Glyoxalines with Picryl Chloride and 2:4–Dinitrochlorobenzene", 1942, pp. 383–386, Journal Of The Chemical Society.

*Primary Examiner*—Robert Gerstl
*Attorney, Agent, or Firm*—Burgess, Ryan & Wayne

[57] ABSTRACT

This invention relates to methods for substitution of an amino group of a heterocyclic primary amine by a chlorine atom and synthesis of 2-chloro-5-methylthiazole and its derivatives by application thereof.

Typically, a heterocyclic primary amine and sodium nitrite are caused to react in the presence of hydrochloric acid, followed by heating the formed diazonium base at 30°–100° C. in the presence of an equimolar or more of hydrochloric acid to substitute the amino group by the chlorine atom. Further, 2-amino-5-methylthiazole and sodium nitrite are caused to react in the presence of hydrochloric acid, followed by heating the formed diazonium base at 30°–100° C. in the presence of an equimolar or over of hydrochloric acid to give 2-chloro-5-methylthiazole. Then, the resultant 2-chloro-5-methylthiazole is caused to react with a chlorinating agent to give 2-chloro-5-chloro-methylthiazole.

6 Claims, No Drawings

METHOD FOR SUBSTITUTION OF AN AMINO GROUP OF A PRIMARY AMINE BY A CHLORINE ATOM AND A SYNTHETIC METHOD BY APPLICATION THEREOF

FIELD OF THE INVENTION

This invention relates to a method for substitution of an amino group in a heterocyclic primary amine by a chlorine atom and a method for the synthesis of 2-chloro-5-methylthiazole derivatives by application thereof.

BACKGROUND OF THE INVENTION

As a method for substitution of an amino group of a primary amine by a chlorine atom, a reaction of an aromatic amine and sodium nitrite in hydrochloric acid to give a diazonium salt followed by Sandmeyer reaction using a Cu(I) salt or Gattermann reaction using an active metallic copper have been known. Diazonium salt formed in the reaction mixture can be substituted by a chlorine atom by heating the reaction mixture as it is, however, the yield of chlorine containing compound is 10% or so in the best. Sandmeyer reaction or Gattermann reaction uses a copper salt or metallic copper, respectively, to improve the yield of chlorine containing compounds. The method using a Cu(I) salt, however, requires equimolar amount of the Cu(I) salt to the amino group and is troublesome for the separation of copper after the reaction. Furthermore, a large amount of copper salt remains to be discarded and requires sufficient care for environmental conditions. Active metallic copper also causes similar problems to those in Cu(I) salt and further requires a process for the preparation of metallic copper which complicates the procedure. Thus, these procedures are unsuitable for industrial scale production. Furthermore, the reaction using copper salt is followed by an alkaline treatment of the reaction mixture after the reaction and causes precipitations of copper salt which are hardly recovered and isolated from the reaction mixture by filtration due to adhesion to the reaction vessels or the like, and makes the operation difficult. For an example of diazotization of a heterocyclic primary amine and substitution of the amino group by a chlorine atom, a solution containing diazotized 2-amino-5-methylthiazole is poured into hydrochloric acid solution containing a copper(I) salt. The reaction mixture is allowed to stand overnight, made alkaline and steam distilled (J. Chem. Soc., 1942, p.386). However, the reaction is complicated and uses copper salt. As explained above, substitution of an amino group in a heterocyclic primary amine by a chlorine atom using a copper salt is not practical for industrial procedure.

While, methods for the production of a useful compound, 2-chloro-5-chloromethylthiazole, as a synthetic raw material of medicines and agricultural chemicals from chlorine and allyl isothiocyanates [Japanese Published Unexamined Patent Application No. 83079 (1988)] or its derivative [Japanese Published Unexamined Patent Application No. 234864 (1992)] have been proposed. However, the raw materials, allyl isothiocyanates, are expensive and pungent, and hardly recognized suitable for industrial scale production.

The inventors of the present invention focused the attention to find an effective method of substitution of an amino group in a heterocyclic primary amine by a chlorine atom to provide a process suitable for the industrial scale production of 2-chloro-5-chloromethylthiazole from 2-amino-5-methylthiazole, which can be produced at low cost, and eagerly investigated the method for substitution of an amino group in a heterocyclic primary amine by a chlorine atom. Thus, one object of the present invention is to provide a method for the substitution of an amino group in a heterocyclic primary amine by a chlorine atom and a synthetic route using the substitution process for the production of 2-chloro-5-methylthiazole and its derivatives.

SUMMARY OF THE INVENTION

Therefore, the object of the present invention is to provide a method for the substitution of an amino group in a heterocyclic primary amine by a chlorine atom by a reaction of heterocyclic primary amine and sodium nitrite in the presence of hydrochloric acid, and heating the produced diazonium base at 30°–100° C. in the presence of an equimolar or more of hydrochloric acid.

The present invention is typically to provide a synthetic method of 2-chloro-5-methylthiazole by a reaction of 2-amino-5methylthiazole and sodium nitrite in the presence of hydrochloric acid and heating the produced diazonium base at 30°–100° C. in the presence of an equimolar or more of hydrochloric acid.

The other object of the present invention is to provide a method for the syntheses of chloro- and chloromethyl-substituted heterocyclic compounds by a reaction of the amino group in a heterocyclic compound having an amino group and a methyl group as the side chains and sodium nitrite in the presence of hydrochloric acid, and heating the produced diazonium base at 30°–100° C. in the presence of an equimolar or more of hydrochloric acid to substitute the amino group of the primary amine by a chlorine atom, followed by chlorination of said methyl group to give chloro- and chloromethyl-substituted heterocyclic compounds.

The synthetic methods of chloro- and chloromethyl-substituted heterocyclic compounds of the present invention are typically provided for the synthetic method of 2-chloro-5chloromethylthiazole from 2-amino-5-methylthiazole.

DETAILED DESCRIPTION OF THE INVENTION

The inventors of the present invention unexpectedly found that heterocyclic primary amines can be converted into diazonium salts in the presence of hydrochloric acid, and heating the resultant diazonium bases in the presence of an equimolar or more of hydrochloric acid provides substitution of the diazonium base by a chlorine atom in high yield differently from aromatic diazonium salts, and accomplished the present invention.

That is, the present invention provides a method to cause reaction of a heterocyclic primary amine and sodium nitrite in the presence of hydrochloric acid to give a diazonium base and followed by substitution of the resultant diazonium base by a chlorine atom by heating at 30°–100° C. in the presence of an equimolar or more of hydrochloric acid. In addition, the present invention applies the above mentioned reaction to provide a method to cause reaction of 2-amino-5-methylthiazole or its hydrochloride and sodium nitrite in the presence of hydrochloric acid, then the formed diazonium base is heated at 30°–100° C. in the presence of an equimolar or over, preferably 1.05- to 3-fold moles of hydrochloric acid to give 2-chloro-5-methylthiazole, and followed by a reaction with a chlorinating agent to give 2-chloro-5-chloromethylthiazole.

The heterocyclic primary amines of the present invention mean heterocyclic compounds bound with an amino group (-NH$_2$) such as aminothiazole, and free amines or their hydrochlorides are provided for the reaction of the present invention.

In the present invention, the heterocyclic primary amines are converted into diazonium salts. The preparation of the diazonium salts is carried out by a reaction of the heterocyclic primary amines and sodium nitrite in the presence of hydrochloric acid at 10° C. or lower, preferably at −10° to 10° C. The formed diazonium base is heated at 30°–100° C. in the presence of an equimolar or more of hydrochloric acid to give chlorinated heterocyclic compounds in which the diazonium base is substituted by a chlorine atom with yields of 60% or over. The heating temperature lower than 30° C. results in incomplete substitution reaction of amino group into chlorine atom. The presence of 3-fold moles or more of hydrochloric acid to the amino group of primary amine is preferable in the diazotization reaction for the presence of an equimolar or more hydrochloric acid to the formed diazonium base. The resultant reaction mixture is extracted with a suitable solvent such as chloroform to give heterocyclic compounds in which the amino group is substituted into chlorine atom. While, if the reaction is carried out in the presence of metallic copper or a copper salt in a similar manner with those of aromatic diazonium salts, the yield will become very low.

Practically, 2-amino-5-methylthiazole which is easily obtained from 2-chloropropionaldehyde and thiourea is diazotized in hydrochloric acid and the resultant reaction mixture containing the diazonium salt is heated in the presence of equimolar or more of hydrochloric acid to the formed diazonium base at 30°–100° C. to give 2-chloro-5-methylthiazole.

Then, 2-chloro-5-methylthiazole is caused to react with a chlorinating agent to chlorinate 5-methyl group and to give 2chloro-5-chloromethylthiazole. The diazotization and chlorination with the chlorinating agent may be carried out successively. The chlorinating agent such as N-chlorosuccinimide and chlorine can be used.

N-Chlorosuccinimide used for the chlorination is preferably used at 0.8–2.0 moles to one mole of 2-chloro-5-methylthiazole. When a large excess amount of N-chlorosuccinimide is used, the formation of by-product increases and causes declined purity of the chlorinated compound in isolation procedure. Various solvents can be used for the reaction and chloroform is suitable since it hardly reacts with the chlorinating agent. The reaction is carried out at a temperature of 20° C. or higher and at reflux temperature or lower of the solvent used. Reaction temperature at lower than 20° C. slows the reaction rate and is unsuitable. The reaction is preferably carried out under light irradiation and in the presence of a radical initiator such as azobisisobutyronitrile, however, any one procedure may be applied solely.

According to the present invention, the amino group in heterocyclic primary amines can easily be converted into chlorine atom. Furthermore, treatment after the reaction can be performed easily since the reaction is carried out without using a copper salt or metallic copper as those in case of aromatic primary amines. The reaction of the present invention can be performed using inexpensive and easily handled 2-amino-5-methylthiazole as a raw material instead of expensive raw materials such as allyl isothiocyanate, and 2-chloro-5methylthiazole can be synthesized under mild reaction conditions. Thus, the present invention provides useful 2-chloro-5chloromethylthiazole as a raw material for the synthesis of medicines and agricultural chemicals at low cost.

The present invention is practically explained by the following examples and comparative examples. However, the scope of the present invention is not restricted by these examples.

EXAMPLE 1

Synthesis of 2-chloro-5-methylthiazole

In a 300 ml volume three necked flask equipped with a stirrer, a dropping funnel and a thermometer, 20 g of 2-amino5-methylthiazole (0.175 mol), 80 ml of 36% hydrochloric acid (0.931 mol) and 30 ml of water were placed and cooled to −5° C. To the mixture, 14 g of sodium nitrite (0.203 mol) dissolved in 30 ml of water was gradually added dropwise at 0° C. or lower. The reaction mixture was further caused to react for three hours at 0° C. or lower to give the diazonium base. The reaction mixture was heated to 80° C. for three hours and extracted with three 40 ml portions of chloroform to give a chloroform solution containing 2-chloro-5-methylthiazole. The chloroform was removed by atmospheric distillation and remained fraction was distilled under reduced pressure to isolate 16.6 g of 2-chloro-5-methylthiazole (0.124 mol) with a yield of 71%.

Comparative Example 1

Synthesis of 2-chloro-5-methylthiazole

In a 300 ml volume three necked flask equipped with a stirrer, a dropping funnel and a thermometer, 20 g of 2-amino5-methylthiazole (0.175 mol), 35 ml of 36% hydrochloric acid (0.407 mol) and 30 ml of water were placed and cooled to −5° C. To the mixture, 14 g of sodium nitrite (0.203 mol) dissolved in 30 ml of water was gradually added dropwise at 0° C. or lower. The reaction mixture was further caused to react for three hours at 0° C. or lower to give the diazonium base. The reaction mixture was heated to 80° C. for three hours and extracted with three 40 ml portions of chloroform to give a chloroform solution containing 2-chloro-5-methylthiazole. The chloroform was removed by atmospheric distillation and remained fraction was distilled under reduced pressure to isolate 10.3 g of 2-chloro-5-methylthiazole (0.077 mol) with a yield of 44%.

Comparative Example 2

Synthesis of 2-chloro-5-methylthiazole

In a 300 ml volume three necked flask equipped with a stirrer, a dropping funnel and a thermometer, 20 g of 2-amino5-methylthiazole (0.175 mol), 23 ml of 36% hydrochloric acid (0.267 mol) and 30 ml of water were placed and cooled to −5° C. To the mixture, 14 g of sodium nitrite (0.203 mol) dissolved in 30 ml of water was gradually added dropwise at 0° C. or lower. The reaction mixture was further caused to react for three hours at 0° C. or lower to give the diazonium base. The reaction mixture was heated to 80° C. for three hours and extracted with three 40 ml portions of chloroform to give a chloroform solution containing 2-chloro-5-methylthiazole. Chloroform was removed by atmospheric distillation and remained fraction was distilled under reduced pressure to isolate 5.1 g of 2-chloro5-methylthiazole (0.038 mol) with a yield of 22%

Comparative Example 3

Synthesis of 2-chloro-5-methylthiazole

In a 300 ml volume three necked flask equipped with a stirrer, a dropping funnel and a thermometer, 20 g of 2-amino5-methylthiazole (0.175 mol), 80 ml of 36% hydrochloric acid (0.931 mol) and 30 ml of water were placed and cooled to −5° C. To the mixture, 14 g of sodium nitrite (0.203 mol) dissolved in 30 ml of water was gradually added dropwise at 0° C. or lower. The reaction mixture was further caused to react for three hours at 0° C. or lower to give the diazonium base solution.

In a 300 ml volume three necked flask equipped with a stirrer, a dropping funnel and a thermometer, 17.3 g of copper(I) chloride (0.175 mol) and 80 ml of 36% hydrochloric acid were placed and cooled to −5° C. In the resultant aqueous solution, the diazonium base solution was gradually added dropwise at 0° C. or lower. The reaction mixture was further caused to react for three hours at 0° C. or lower and heated at 80° C. for further three hours. After the reaction, the reaction mixture was made alkaline by addition of 15% sodium hydroxide aqueous solution and the precipitated copper salt was removed by filtration. The resulting filtrate was extracted with three 40 ml portions of chloroform to give a chloroform solution containing 2-chloro-5-methylthiazole. The chloroform was removed by atmospheric distillation and remained fraction was distilled under reduced pressure to isolate 8.4 g of 2-chloro-5-methylthiazole (0.063 mol) with a yield of 36%

EXAMPLE 2

Synthesis of 2-chloro-5-chloromethylthiazole

In a 200 ml volume three necked flask equipped with a stirrer, a dropping funnel and a thermometer, 14 g of 2-amino5-methylthiazole hydrochloride (0.093 mol), 25 ml of 36% hydrochloric acid and 20 ml of water were place and cooled to −5° C. To the mixture, 6.8 g of sodium nitrite (0.0986 mol) dissolved in 10 ml of water was gradually added dropwise at 0° C. or lower. The reaction mixture was further caused to react for one hour at 0° C. or lower to give the diazonium base. The reaction mixture was heated to 40° C. for three hours and extracted with three 40 ml portions of chloroform to give a chloroform solution containing 2-chloro-5-methylthiazole. The chloroform was removed by atmospheric distillation and remained fraction was distilled under reduced pressure to isolate 10.1 g of 2-chloro-5-methylthiazole (0.0756 mol) with a yield of 81%.

The resulting 2-chloro-5-methylthiazole was dissolved in 20 ml of chloroform and placed in a 100 ml volume three necked flask equipped with a stirrer, a high pressure mercury lamp and a thermometer. Then, 10 g of N-chlorosuccinimide (0.0749 mol) was added and the reaction mixture was caused to react at 50° C. for six hours under light irradiation. After the reaction, 30 ml of water was added to recover by-produced succinimide and separated chloroform layer was evaporated to give 9.5 g of 2chloro-5-chloromethylthiazole (0.0565 mol) with a yield of 61%.

The recovered succinimide was chlorinated to give N-chlorosuccinimide and reused.

EXAMPLE 3

Synthesis of 2-chloro-5-chloromethylthiazole

In a 300 m volume three necked flask equipped with a stirrer, a dropping funnel and a thermometer, 20 g of 2-amino5-methylthiazole (0.175 mol), 80 ml of 36% hydrochloric acid (0.931 mol) and 40 ml of water were placed and cooled to −5° C. To the mixture, 14 g of sodium nitrite (0.203 mol) dissolved in 30 ml of water was gradually added dropwise at 0° C. or lower. The reaction mixture was further caused to react for three hours at 0° C. or lower to give the diazonium base. The reaction mixture was heated to 80° C. for three hours and extracted with three 40 ml portions of chloroform to give a chloroform solution containing 17.4 g of 2-chloro-5-methylthiazole (0.130 mol).

The resulting 2-chloro-5-methylthiazole chloroform solution was placed in a 200 ml volume three necked flask equipped with a stirrer, a high pressure mercury lamp and a thermometer. Then, 26.7 g of N-chlorosuccinimide (0.200 mol) and 0.4 g of azobisisobutyronitrile were added and the reaction mixture was caused to react at 50° C. for 10 hours under light irradiation.

After the reaction, 120 ml of water was added to recover by-produced succinimide and separated chloroform layer was evaporated to give 15.5 g of 2-chloro-5-chloromethylthiazole (0.092 mol) with a yield of 53%.

The recovered succinimide was chlorinated to give N-chlorosuccinimide and reused.

EXAMPLE 4

Synthesis of 2-chloro-5-chloromethylthiazole

In a 300 ml volume three necked flask equipped with a stirrer, a dropping funnel and a thermometer, 26.2 g of 2-amino-5-methylthiazole hydrochloride (0.175 mol), 80 ml of 36% hydrochloric acid (0.931 mol) and 40 ml of water were placed and cooled to −5° C. To the mixture, 14 g of sodium nitrite (0.203 mol) dissolved in 30 ml of water was gradually added dropwise at 0° C. or lower. The reaction mixture was further caused to react for three hours at 0° C. or lower to give the diazonium base. The reaction mixture was heated to 80° C. for three hours and extracted with three 40 ml portions of chloroform to give a chloroform solution containing 15.1 g of 2chloro-5-methylthiazole (0.113 mol).

The resultant 2-chloro-5-methylthiazole chloroform solution was placed in a 200 ml volume three necked flask equipped with a stirrer, a high pressure mercury lamp and a thermometer. Then, 16.0 g of N-chlorosuccinimide (0.120 mol) and 0.4 g of azobisisobutyronitrile were added and the reaction mixture was caused to react at 50° C. for 10 hours under light irradiation.

After the reaction, 100 ml of water was added to remove by-produced succinimide and separated chloroform layer was evaporated to give 13.5 g of 2-chloro-5-chloromethylthiazole (0.080 mol) with a yield of 46%.

The recovered succinimide was chlorinated to give N-chlorosuccinimide and reused.

We claim:

1. A method for synthesis of 2-chloro-5-methylthiazole which consists essentially of reacting 2-amino-5-methylthiazole and sodium nitrite in the presence of hydrochloric acid, followed by heating the formed diazonium base at 30°–100° C. in the presence of an equimolar or over of hydrochloric acid.

2. A method for synthesis of 2-chloro-5-chloromethylthiazole which consists essentially of reacting 2-amino-5-methylthiazole and sodium nitrite in the presence of hydrochloric acid, followed by heating the formed diazonium base at 30°–100° C. in the presence of an equimolar or over of hydrochloric acid to give 2chloro-5-methylthiazole and then reacting with a chlorinating agent.

3. The method according to claim 2 wherein the reaction with chlorinating agent is carried out in chloroform.

4. The method according to claim 2 wherein the reaction with the chlorinating agent is carried out under light irradiation and/or in the presence of a radical initiator.

5. The method according to claim 3 wherein the reaction with the chlorinating agent is carried out under light irradiation and/or in the presence of a radical initiator.

6. A method for synthesis of 2-chloro-5-chloromethylthiazole which consists essentially of reacting 2-amino-5-methylthiazole and sodium nitrite in the presence of hydrochloric acid, followed by heating the formed diazonium base at 30°–100° C. in the presence of an equimolar or over of hydrochloric acid to give 2chloro-5-methylthiazole and, then, reacting with N-chlorosuccinimide under light irradiation and/or in the presence of a radical initiator to give 2-chloro-5-chloromethylthiazole, thereafter by-produced succinimide is recovered in aqueous layer by adding water to the reaction mixture and the recovered succinimide is chlorinated for reuse.

* * * * *